United States Patent
Pettibone et al.

(10) Patent No.: US 9,970,873 B1
(45) Date of Patent: May 15, 2018

(54) SYSTEM AND METHOD FOR LUMINESCENT TAG BASED WAFER INSPECTION

(71) Applicant: KLA-Tencor Corporation, Milpitas, CA (US)

(72) Inventors: Donald Pettibone, San Jose, CA (US); Chuanyong Huang, San Jose, CA (US); Kurt Haller, Pleasanton, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days. days.

(21) Appl. No.: 14/939,959

(22) Filed: Nov. 12, 2015

Related U.S. Application Data

(60) Provisional application No. 62/078,906, filed on Nov. 12, 2014.

(51) Int. Cl.
  *G01N 21/00* (2006.01)
  *G01N 21/64* (2006.01)
  *G01N 21/95* (2006.01)

(52) U.S. Cl.
  CPC ....... *G01N 21/643* (2013.01); *G01N 21/9501* (2013.01); *G01N 2021/6439* (2013.01)

(58) Field of Classification Search
  CPC .. G01N 21/00; G01N 21/643; G01N 21/9501; G01N 2021/6439

(Continued)

(56) References Cited

U.S. PATENT DOCUMENTS

| 6,014,209 A | 1/2000 | Bishop |
|---|---|---|
| 6,091,488 A | 7/2000 | Bishop |

(Continued)

FOREIGN PATENT DOCUMENTS

| CN | 101493425 B | 7/2009 |
|---|---|---|

OTHER PUBLICATIONS

Stefano Corni et al., Conformational Behavior of Genetically-Engineered Dodecapeptides as a Determinant of Binding Affinity for Gold, The Journal of Physical Chemistry, Aug. 8, 2013, pp. 16990-17003, vol. 117, Issue 33, American Chemical Society, United States.

(Continued)

*Primary Examiner* — Brian J. Sines
(74) *Attorney, Agent, or Firm* — Suiter Swantz pc llo

(57) ABSTRACT

A luminescent tag based defect detection system comprises a luminescent tag attachment assembly, an illumination source, one or more detectors, and a set of optical elements. The luminescent tag attachment assembly exposes a sample to one or more luminescent tag materials selectively attached to one or more defects on the sample. The illumination source generates illumination including one or more wavelengths corresponding to the one or more absorption spectra associated with the one or more luminescent tags. At least a portion of the set of optical elements directs illumination from the illumination source to the sample, and at least a portion of the set of optical elements directs illumination emitted from the one or more luminescent tag materials to the one or more detectors. A luminescent tag based defect detection system may also include a luminescent tag removal assembly to remove the luminescent tags after detection.

31 Claims, 7 Drawing Sheets

(58) Field of Classification Search
USPC .................................. 422/82.05; 436/172
See application file for complete search history.

(56) References Cited

U.S. PATENT DOCUMENTS

| | | | |
|---|---|---|---|
| 6,335,531 B1 | 1/2002 | Somerville et al. | |
| 6,630,996 B2 | 10/2003 | Rao et al. | |
| 6,665,065 B1 | 12/2003 | Phan et al. | |
| 6,775,051 B2 | 8/2004 | Sullivan et al. | |
| 6,791,099 B2 | 9/2004 | Some et al. | |
| 6,891,627 B1 | 5/2005 | Levy et al. | |
| 7,230,335 B2 | 6/2007 | Cann et al. | |
| 7,676,077 B2 | 3/2010 | Kulkarni et al. | |
| 8,571,299 B2 | 10/2013 | Fayaz et al. | |
| 8,995,746 B2 | 3/2015 | Cao et al. | |
| 2009/0016595 A1* | 1/2009 | Peterson | G03F 1/84 382/144 |
| 2011/0271257 A1 | 11/2011 | Terris et al. | |
| 2012/0126141 A1* | 5/2012 | Pulisciano | G01B 11/25 250/459.1 |
| 2013/0035876 A1* | 2/2013 | Huang | G01N 21/9501 702/40 |
| 2014/0050389 A1* | 2/2014 | Mahadevan | G06T 7/0004 382/149 |

OTHER PUBLICATIONS

Kastrup et al., Absolute Optical Cross Section of Individual Fluorescent Molecules, Angewandte Chemie, Nov. 19, 2004, pp. 2-5, vol. 43, Issue 48, Wiley-VCH Verlag GmbH & Co. KGaA, Weinheim.

Love et al., Self-Assembled Monolayers of Thiolates on Metals as a Form of Nanotechnology, Chemical Reviews, Mar. 25, 2005, pp. 1103-1169, vol. 105, No. 4, American Chemical Society, Published on Web.

Li Shang et al., Fluorescent Conjugated Polymer-Stabilized Gold Nanoparticles for Sensitive and Selective Detection of Cysteine, The Journal of Physical Chemistry C, Aug. 2007, pp. 13414-13417, vol. 111, Issue 36, American Chemical Society.

Dinesh Shenoy et al., Surface functionalization of gold nanoparticles using hetero-bifunctional poly(ethylene glycol) spacer for intracellular tracking and delivery, International Journal of Nanomedicine, Mar. 2006, pp. 51-57, vol. 1, Issue 1, Dove Medical Press Limited.

Myung M. Sung et al., Self-Assembled Monolayers of Alkanethiols on Clean Copper Surfaces, Bulletin of the Korean Chemical Soc., 2001, pp. 748-752, vol. 22, No. 7.

Jingyue Ju et al., Four-color DNA sequencing by synthesis using cleavable fluorescent nucleotide reversible terminators, PNAS, Dec. 26, 2006, pp. 19635-19640, vol. 103, No. 52, The National Academy of Sciences of the USA.

* cited by examiner

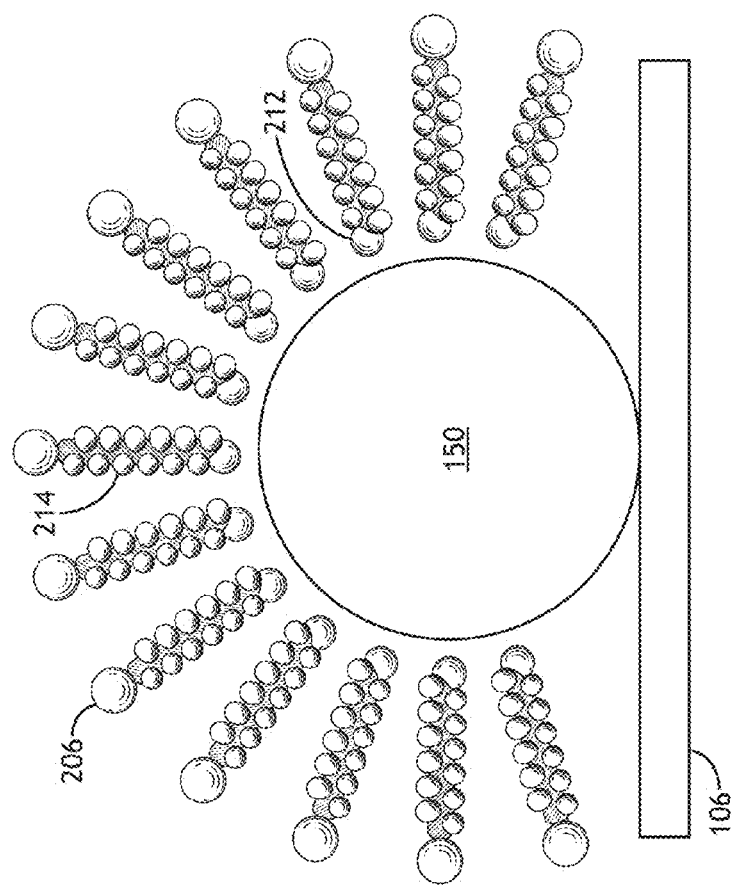

SYSTEM AND METHOD FOR LUMINESCENT TAG BASED WAFER INSPECTION

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC § 119(e) for provisional patent applications, for any and all parent, grandparent, great-grandparent, etc. applications of the Related Application(s)).

RELATED APPLICATIONS

For purposes of the USPTO extra-statutory requirements, the present application constitutes a regular (non-provisional) patent application of United States Provisional Patent Application entitled Fluorescent tag based wafer inspection, naming Don Pettibone and Chuanyong Huang as inventors, filed Nov. 12, 2014, Application Ser. No. 62/078,906.

TECHNICAL FIELD

The present disclosure relates generally to the detection of defects on a semiconductor wafer, and, in particular, to use of luminescent tags to selectively bind to defects.

BACKGROUND

Wafer inspection systems are often used to analyze wafers to determine the presence of defects on a wafer. Many wafer inspection systems detect defects using dark field optical systems in which illumination is scattered from defect sites. A drive to detect increasingly smaller defects generates challenges to current detection systems. A first challenge is that the strength of scattered illumination scales as the sixth power of the radius of the scattering object. Thus, decreasing the radius of a scattering object by a factor of two results in a decrease in the strength of scattered illumination by a factor of 64. A second challenge is that that wafer surface roughness and scattering from air molecules (e.g. $N_2$, $O_2$, $CO_2$, and the like), generates a background signal that limits the size of detectable defects. A third challenge is that technological hurdles may limit the ability to scale the wavelength of an illumination source to lower wavelengths in order to increase scattering strength. Therefore, there exists a critical need to develop systems and methods to detect small particles in wafer inspection systems.

SUMMARY

A luminescent tag based defect detection system is disclosed, in accordance with one illustrative embodiment of the present disclosure. In one illustrative embodiment, the system includes a luminescent tag attachment assembly configured to expose a sample to one or more luminescent tag materials. In another illustrative embodiment, the one or more luminescent tag materials absorb illumination within one or more absorption spectra and emit illumination within one or more emission spectra. In another illustrative embodiment, the one or more luminescent tags selectively attach to one or more defects on the sample. In another illustrative embodiment, the system includes an illumination source configured to generate illumination including one or more wavelengths corresponding to the one or more absorption spectra. In another illustrative embodiment, the system includes one or more detectors. In another illustrative embodiment, the system includes a set of optical elements. In another illustrative embodiment, at least a portion of the set of optical elements directs illumination from the illumination source to the sample. In another illustrative embodiment, at least a portion of the set of optical elements collects illumination from the sample. In another illustrative embodiment, at least a portion of the set of optical elements directs illumination emitted from the one or more luminescent tag materials to the one or more detectors.

An apparatus is disclosed, in accordance with one illustrative embodiment of the present disclosure. In one illustrative embodiment, the apparatus includes a luminescent tag attachment assembly. In another illustrative embodiment, the luminescent tag attachment assembly is configured to expose a sample to one or more luminescent tag materials. In another illustrative embodiment, the one or more luminescent tag materials absorb illumination within one or more absorption spectra and emit illumination within one or more emission spectra. In another illustrative embodiment, the one or more luminescent tag materials selectively attach to one or more defects on the sample.

A method to detect defects on a sample using luminescent tag materials is disclosed, in accordance with one illustrative embodiment of the present disclosure. In one illustrative embodiment, the method includes exposing the sample to one or more luminescent tag materials. In another illustrative embodiment, the one or more luminescent tag materials absorb illumination within one or more absorption spectra and emit illumination within one or more emission spectra. In another illustrative embodiment, the one or more luminescent tag materials selectively attach to one or more defects on the sample. In one illustrative embodiment, the method includes illuminating the sample. In another illustrative embodiment, the illumination includes one or more wavelengths corresponding to the one or more absorption spectra. In one illustrative embodiment, the method includes detecting luminescent illumination emitted by the one or more luminescent tag materials. In one illustrative embodiment, the method includes identifying the one or more defects based on the detected luminescent illumination.

BRIEF DESCRIPTION OF DRAWINGS

FIG. 2C is a simplified schematic illustrating multiple luminescent tags selectively bound to a particle defect on a wafer, in accordance with one or more embodiments of the present disclosure.

DETAILED DESCRIPTION

Figure 1A:
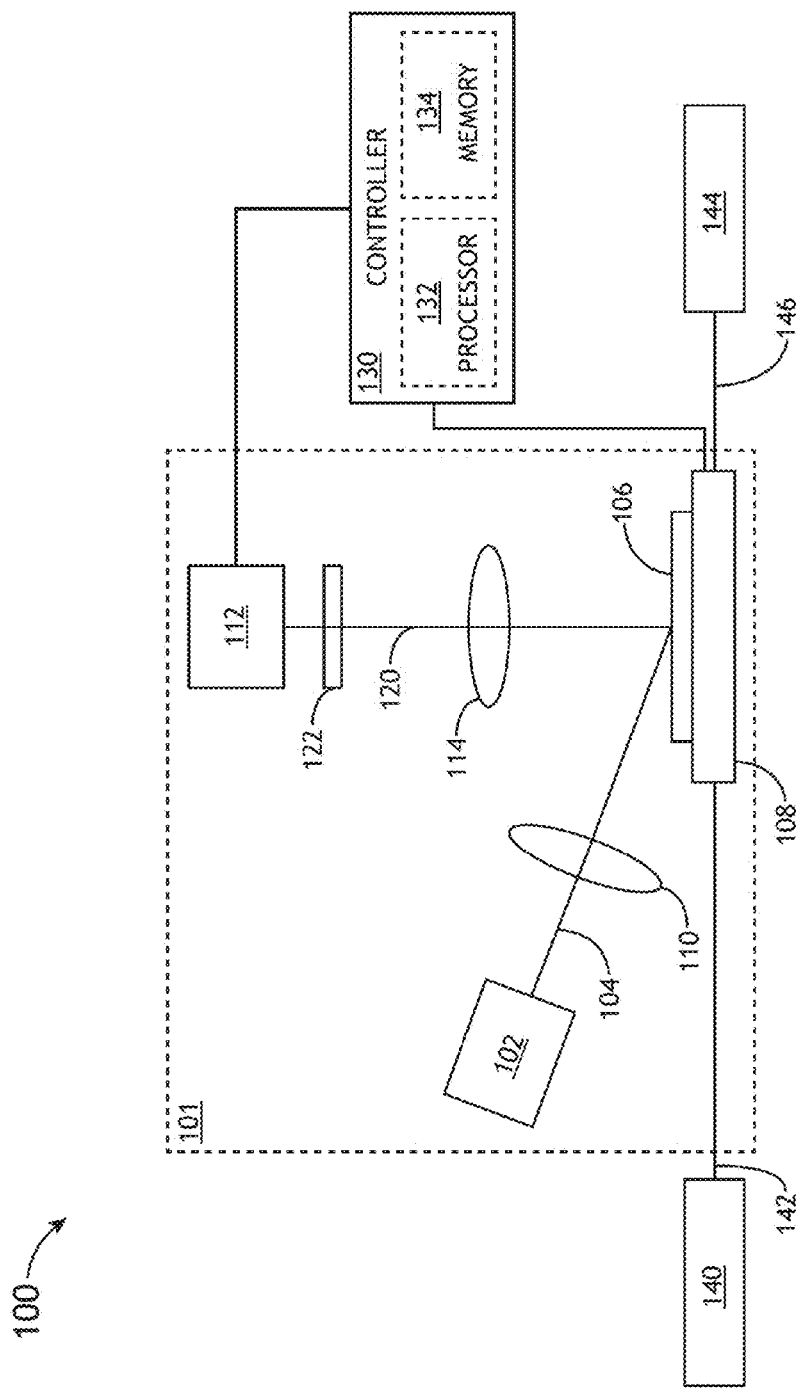
FIG. 1A is a conceptual schematic of a luminescent tag based inspection system, in accordance with one or more embodiments of the present disclosure.

Reference will now be made in detail to the subject matter disclosed, which is illustrated in the accompanying drawings. The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

Referring generally to FIGS. 1 through 4, a system and a method for luminescent tag based defect detection of defects on a wafer surface is disclosed, in accordance with one or more embodiments of the present disclosure. It is recognized herein that a luminescent molecule emits illumination without the addition of heat and that there are multiple types of luminescent molecules such as, but not limited to, photoluminescent molecules, which emit illumination in response to the absorption of one or more photons, and chemiluminescent molecules, which emit illumination in response to a chemical reaction. In one embodiment, a luminescent tag includes a fluorescent molecule (hereinafter referred to as a fluorophore). In another embodiment, a luminescent tag includes a phosphorescent molecule. In another embodiment, a luminescent tag includes a chemiluminescent molecule.

It is further recognized that a photoluminescent molecule may have an absorption spectrum (e.g., a range of wavelengths) such that the absorption of illumination with a wavelength in this band excites the molecule into an excited state. It is noted herein that the excited state may include excited electronic state, and an excited vibrational state. The luminescence of a photoluminescent molecule is then a radiative emission of illumination associated with a transition of the photoluminescent molecule back to a lower state (e.g. a ground state). It is further noted that many photoluminescent molecules undergo non-radiative transitions (e.g. vibrational relaxations) in addition to a radiative transition. Thus, a photoluminescent molecule will emit radiation with a lower energy (longer wavelength) than absorbed. In this regard, the emission spectrum of a photoluminescent molecule is distinct from the absorption spectrum. For example, luminescent emission associated with a fluorescent molecule (e.g. fluorescence) is associated with a radiative decay of electrons from an excited electronic state to a lower electronic state, which may occur within lifetimes of on the order of nanoseconds. As another example, luminescent emission associated with a phosphorescent molecule is associated with a radiative decay of electrons from an excited triplet state. It is noted that excited electrons within a phosphorescent molecule may enter a triplet state through a non-radiative decay associated with a change of electron spin; the lifetime associated with the radiative decay of electrons from an excited triplet state may be on the order of milliseconds up to multiple hours.

Embodiments of the present disclosure are directed to exposing a wafer to luminescent tags (e.g. luminescent tag materials) such that the luminescent tags selectively bind to defect sites on the wafer such that defects are identified based on the detection of luminescent light emitted by the luminescent tags. Additional embodiments are directed to identifying the size and shape of defect sites by the strength of fluorescent illumination emitted from the defect sites. Additional embodiments are directed to the removal of the luminescent tags from the wafer surface. A spot scanning wafer inspection system is generally described in U.S. Pat. No. 6,775,051 issued on Aug. 10, 2004; and U.S. Pat. No. 8,995,746 filed on Mar. 31, 2015; which are incorporated herein by reference in their entirety.

Figure 1B:
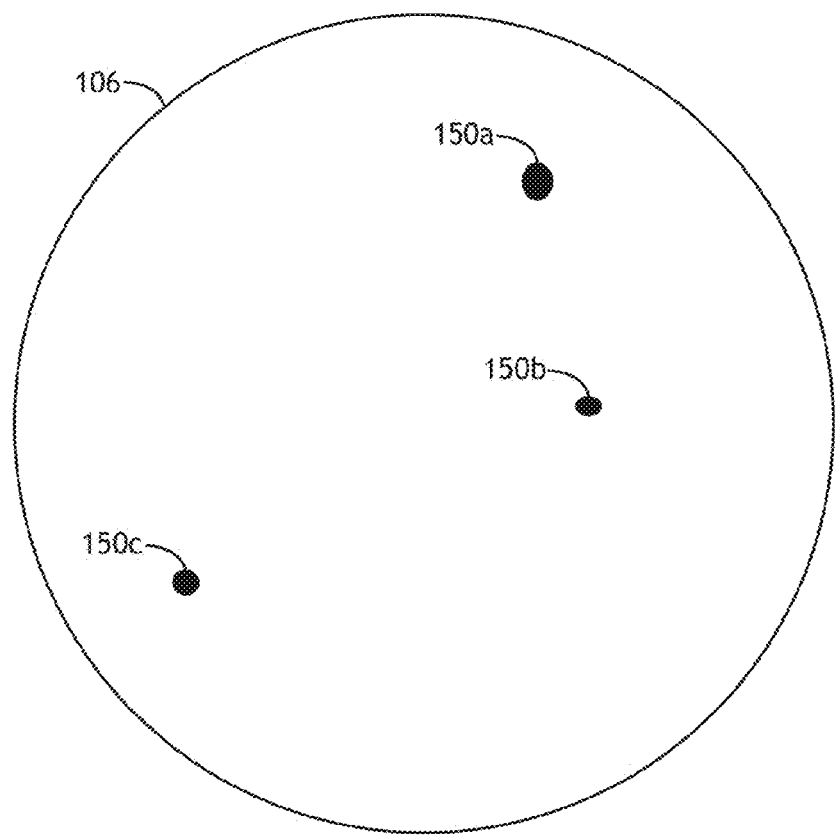
FIG. 1B is a conceptual schematic of a wafer including three defects, in accordance with one or more embodiments of the present disclosure.

FIG. 1A is a simplified schematic diagram illustrating a luminescent tag based wafer inspection system 100, in accordance with one or more embodiments of the present disclosure. FIG. 1B is a simplified schematic diagram illustrating defects 150a, 150b, and 150c on a wafer 106, in accordance with one or more embodiments of the present disclosure. It is noted herein that the defects 150 illustrated in FIG. 1B are shown at a high magnification for illustrative purposes.

Defects 150 detectable by a luminescent tag inspection system 100 in an inspection system 100 may include, but are not limited to, structural defects in a wafer 106 or foreign materials on the surface of a wafer 106. For example, structural defects 150 may include, but not limited to, pits or cracks in the surface of a wafer 106. As another example, foreign materials on the surface of a wafer 106 may include, but are not limited to metals, metal oxides, metal nitrides, semiconductor oxides, semiconductor nitrides, polymers, or combinations thereof. In one embodiment, the system 100 is configured to detect adder defects associated with foreign particles generated during a manufacturing process. For example, adder defects may include metal particles such as, but not limited to, copper, aluminum, cobalt, titanium, iron, nickel, chromium, gold, or silver particles. It is noted herein that the non-limiting examples of copper, aluminum, cobalt, titanium, iron, nickel, or chromium may constitute adder particles associated with front-end silicon integrated circuit processing systems and that the non-limiting examples of gold or silver may be constitute adder particles associated with back-end packaging of one or more wafers 106.

A luminescent tag based inspection system 100 may be configured to detect defects 150 on any type of surface known in the art including, but not limited to, an unpatterned wafer, a film, or a patterned wafer. The system 100 may additionally detect defects down to 1-2 nm in size. It is noted herein that the absorption cross section and quantum yield of a luminescent molecule may be larger than the scattering cross section of a defect site, which may reduce the intensity of illumination necessary to detect defects 150 of a given size.

Figure 2A:
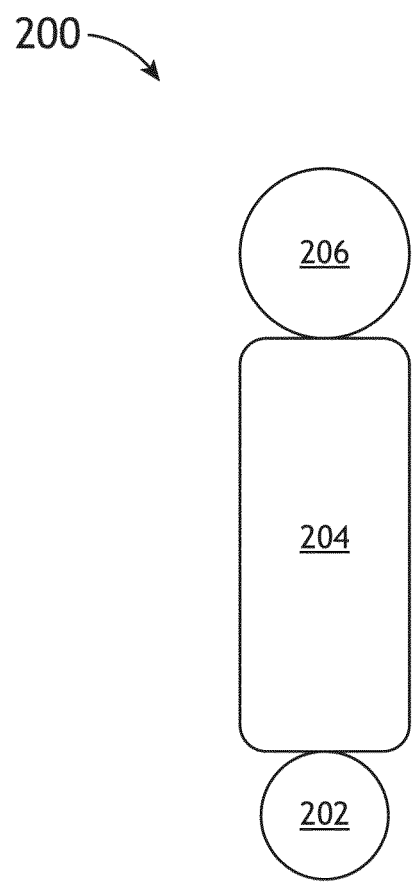
FIG. 2A is a simplified schematic illustrating a luminescent tag including a luminescent molecule, a linker molecule, and a binder molecule, in accordance with one or more embodiments of the present disclosure.

Luminescent tags utilized in a luminescent tag based wafer inspection system 100 may include any type of luminescent tags known in the art suitable for selectively binding to one or more defects 150. A luminescent tag may include multiple functional groups. In one embodiment, a luminescent tag includes a luminescent molecule and a binder molecule suitable for selectively binding the luminescent tag to a defect site. In another embodiment, a luminescent tag includes a luminescent molecule, a binder molecule, and a linker molecule. FIG. 2A is a simplified schematic illustrating a luminescent tag 200 including a luminescent molecule 206, a linker molecule 204, and a binder molecule 202, in accordance with one or more embodiments of the present disclosure. It is noted herein that a linker molecule 204 may be used to functionally and/or physically separate a luminescent molecule 206 from a binder molecule 202 to maximize the efficiency of the fluorescent properties of the luminescent molecule 206. The length of the linker molecule 204 may be adjusted to balance the physical separation of a luminescent molecule 206 from other molecules that may induce quenching of the luminescent output and the physical separation of the luminescent molecule 206 from the defect site of interest. Since the luminescent tag based inspection system 100 detects defects 150 based on the detection of luminescent illumination, the size and shape of a defect 150 may be associated with the physical size and shape of one more luminescent tags 200 attached to the defect sites. A luminescent tag 200 may selectively attach to one or more defects 150 in any number of arrangements including, but not limited to, a monolayer, a bilayer, or a multilayer. A luminescent tag 200 in a luminescent tag based inspection system 100 may include any type of linker molecule 204 known in the art suitable for separating a luminescent molecule 206 from a quenching molecule or for providing a link between a luminescent molecule 206 and a binder molecule 202. For example, a linker molecule 204 may include, but is not limited to, a linear alkane, polyethylene glycol (PEG), an inorganic polymer, or a polypeptide.

A luminescent tag 200 in a luminescent tag based wafer inspection system 100 may include any type of luminescent particle known in the art suitable for generating luminescence, attaching to a defect 150 and/or attaching to additional functional groups within the luminescent tag. In one embodiment, one or more luminescent tags 200 include one or more fluorescent tags. For example, a luminescent tag 200 may include fluorescent particles such as, but not limited to quantum dots, which may have a size less than 10 nm. For example, a fluorescent tag may include fluorescent proteins including, but not limited to, green fluorescent protein (GFP), red fluorescent protein (RFP), or yellow fluorescent protein (YFP). As another example, a fluorescent tag may include non-protein fluorophores including, but not limited to coumarin derivatives (e.g. methylcoumarin), xanthene derivatives (e.g. fluorescein), or pyrene derivatives (e.g. cascade blue). It is noted that each fluorophore has a unique absorption and emission spectrum and that selection of one or more fluorophores in a wafer inspection system may be chosen such that the absorption spectra overlap the wavelength of the illumination source 102. In one embodiment, the system 100 utilizes one or more fluorescent tags 200 with overlapping absorption spectra such that a single illumination source 102 may simultaneously excite the one or more fluorescent tags 200. In another embodiment, the system 100 utilizes one or more fluorescent tags with distinct absorption spectra such that multiple illumination sources 102 excite the one or more fluorescent tags. It is further noted that one or more fluorescent tags with distinct emission spectra bound with high specificity to distinct defect types may enable the simultaneous detection of multiple defect types based on the detection of fluorescent illumination. It is noted that the description of fluorescence in the present disclosure is intended to be illustrative rather than limiting and that detection of defects using any type of luminescent material is within the scope and spirit of the present disclosure. In one embodiment, the system 100 detects one or more defects 150 using one or more phosphorescent tags selectively attached to the one or more defects 150.

A luminescent tag 200 in a luminescent tag based inspection system 100 may include any binder molecule known in the art suitable for selectively binding a luminescent molecule 206 to a defect 150. It is noted herein that the binder molecule may be tailored for specific defect types. In one embodiment, one or more luminescent tags 200 include one or more ligands suitable for binding to a metallic particle defect 150 on a wafer 106. For example, one or more luminescent tags 200 may include, but is not limited to, a thiol. In one embodiment, one or more luminescent tags include an alkanethiol (e.g. $CH_3(CH_2)_{n-1}SH$) suitable for selectively binding to metallic particles such as, but not limited to, copper particles as described in: Sung. et al, Bull. Korean Chem. Soc. Vol 22, No. 7, pp 748-752 (2001), which is incorporated herein by reference. It is noted herein that thiols such as, but not limited to, alkanethiols, may be strongly chemisorbed onto metallic surfaces through the formation of covalent-like bonds between the sulfur atom and the metal.

It is further noted that thiols may provide a high degree of specificity such that the luminescent tags 200 are strongly preferentially bound to metallic particle defects 150 over the surrounding wafer 106. A high degree of specificity is required to achieve a low rate of false-positives associated with luminescent tags 200 binding to non-defect site on a wafer 106. Specificity may be attributed in part to chemical differences between metallic particle defects 150 and the surrounding wafer 106, which may be formed from, but is not limited to, bare semiconductor materials or a native oxide. For example, it is noted that herein that the top surface of a semiconductor with a native oxide layer may include a prevalence of oxygen sites, which may tend to have a higher affinity to acidic molecules with available hydrogen bonds. It is noted herein that a thiol may bind to a surface by breaking the sulfur-hydrogen bond and generating a bond between the remaining sulfur atom and the surface. For example, a metallic particle defect 150 may break the sulfur-hydrogen bond of the thiol more readily than the surrounding wafer 106, resulting in preferential attachment of the thiol to a metallic particle relative to the surrounding wafer 106. As another example, defects 150 consisting of organic matter containing thiol functional groups may be tagged with reactive binders including, but not limited to, iodoacetamides, maleimides, disulfides, or thiosulfates. It is further noted that the disulfide bond formed between a thiosulfate and thiol group may be subsequently broken such that the one or more luminescent tags may be removed after the detection of one or more defects 150.

In many applications, a semiconductor wafer 106 has a native oxide layer, further decreasing the affinity of a thiol group to the wafer 106. In one embodiment, an additional passivation layer may be applied to the surface of a wafer 106 prior to exposure to luminescent tags 200 in order to further increase the specificity at which luminescent tags 200 preferentially bind to defect sites 150 over the wafer 106. For example, the passivation layer may include a hydrophobic coating such as, but not limited to, a silicon or silane layer. As another example, a wafer 106 may be exposed to a solution of hydrofluoric acid to terminate dangling bonds and render the surface of the wafer hydrophobic. In one embodiment, a reducing agent is applied to facilitate preferential binding between a defect 150 and the surrounding wafer 106. For example, some metallic particle defects 150, such as, but not limited to, copper, may have a native oxide layer; removing this oxide layer prior to exposing the wafer 106 to luminescent tags 200 may enhance the selectivity of binding to the one or more defect sites 150.

Figure 2B:
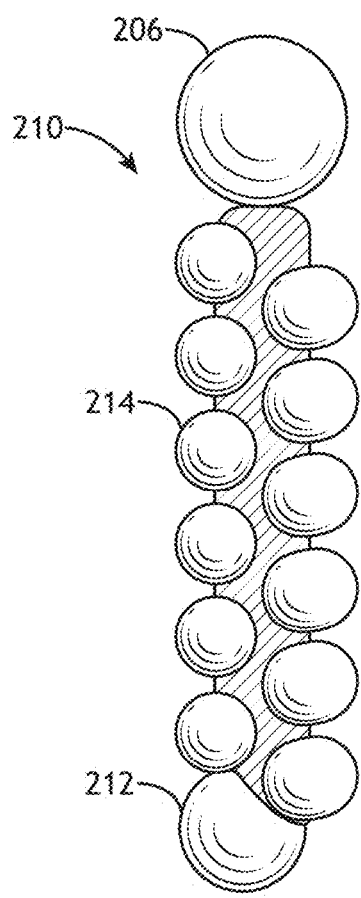
FIG. 2B is a simplified schematic of a luminescent tag including a luminescent molecule and a thiol, in accordance with one or more embodiments of the present disclosure.

Furthermore, thiols may be particularly well suited for forming densely-packed self-assembled monolayers on metal surfaces as described in: Love, et al, Chem. Rev. vol. 25, pp 1103-1169 (2005), which is incorporated herein by reference. FIGS. 2B and 2B are schematic diagrams illustrating the attachment of luminescent tags 210 bound to a defect 150 attached to the surface of a wafer 106, in accordance with one or more embodiments of the present disclosure. FIG. 2C illustrates a single luminescent tag 210 formed from a luminescent molecule 206 and a thiol including a carbon chain 214 (e.g. an alkane or an alkene) and a sulfur bonding site 212. In this way, a densely packed monolayer of luminescent tags including thiol binders may form on a defect 150 as illustrated in FIG. 2C. In this way, the one or more luminescent tags may produce luminescent output correlated to the surface area of the defect 150.

Figure 3:
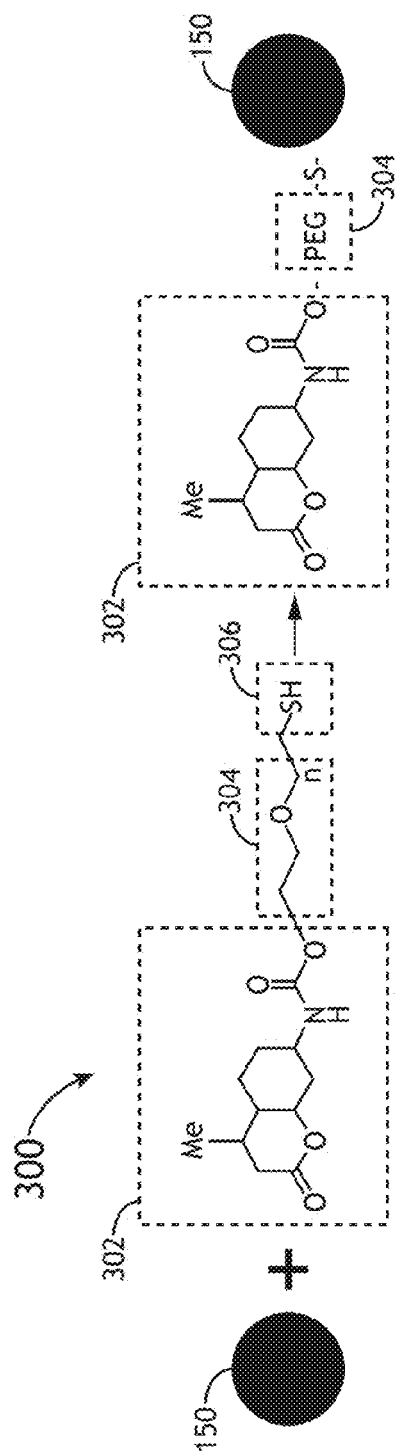
FIG. 3 is a simplified schematic illustrating the attachment of 4 methylcoumarin-PEG-thiol to a particle defect, in accordance with one or more embodiments of the present disclosure.

In another embodiment, one or more luminescent tags are formed from three functional groups including a luminescent molecule, a linker, and a binder. In one embodiment, one or more luminescent tags are formed from 4-methylcoumarin-PEG-thiol. The synthesis of 4-methylcoumarin-PEG-thiol attached to a gold nanoparticle as a fluorescent marker is described in: Shenoy, et al., Int. J. of Nanomedicine, vol. 1, no. 1, pp. 51-57 (2006), which is incorporated herein by reference. It is noted herein that 4-methylcoumarin-PEG-thiol synthesized without gold nanoparticles may be used as a luminescent tag with high affinity to metal particle defects 150. FIG. 3 is an illustrative schematic demonstrating the binding of 4-methylcoumarin-PEG-thiol to a particle defect 150, in accordance with one or more embodiments of the present disclosure. In this way, 4-methylcoumarin 302 is a luminescent molecule exhibiting fluorescence, PEG 304 is a linker, and the thiol 306 is the binder. It is noted that the PEG 304 chain provides physical and chemical separation between the 4-methylcoumarin 302 and the thiol 306. For example, PEG 304 may limit quenching of the fluorescent illumination of 4-methylcoumarin by a metallic particle defect 150. The luminescent tag 300 binds to the defect 150 by breaking the sulfur-hydrogen bond and forming a bond between the sulfur atom and the defect 150. In another embodiment, the linker molecule is a simple alkane.

In one embodiment, one or more luminescent tags include one or more polypeptides. In one embodiment, one or more luminescent tags include dodecapeptides with a high affinity for metallic particle defects 150. For example, one or more luminescent tags may include, but is not limited to, dodecapeptides AuBP1 or AuBP2 having high affinities for gold. AuBP1 includes an amino acid sequence of WAGAKRLVLRRE and AuBP2 includes an amino acid sequence of WALRRSIRRQSY, where W corresponds to tryptophan, A corresponds to tlanine, G corresponds to glycine, K corresponds to lysine, R corresponds to arginine, L corresponds to leucine, V corresponds to valine, E corresponds to glutamic acid, S corresponds to serine, I corresponds to isoleucine, Q corresponds to glutamine, and Y corresponds to tyrosine.

It is noted herein that polypeptides may be tailored to have a high affinity for a specific material type and thus may operate with high specificity in a luminescent tag based inspection system 100. For example, differences in binding mechanisms between dodecapeptides tailored to have a high affinity for gold (e.g. AuBP1 and AuBP2) were compared to dodecapeptides tailored to have a high affinity for quartz (e.g. QBP1) are described in: Corni, et al, J. of Phys. Chem. C, vol. 117, pp 16990-17003 (2013), which is incorporated herein by reference. Specifically, the dodecapeptides AuBP1, AuBP2, and QBP1 were developed through biocombinatorial synthesis techniques to have high affinities for specific materials. In this way, one or more types of defects 150 such as, but not limited to, gold particles, copper particles, silver particles, or organic materials may be detected by one or more luminescent tags including polypeptides with tailored affinities.

In one embodiment, one or more luminescent tags include one or more organic functional groups tailored to bind to organic functional groups associated with one or more defects 150. For example, one or more luminescent tags may include an amine functional group suitable for binding with, but not limited to, isothiocyanates, succinimidyl esters, carboxylic esters, or sulfonyl chlorides. In another embodiment, one or more luminescent tags with a hydrophobic binder are tailored to selectively bind to hydrophobic organic matter such as, but not limited to, saturated polymers including ultra-high-molecular-weight polyethylene. In this regard, a sufficiently hydrophobic luminescent tag will have a higher affinity for a hydrophobic defect 150 than for a surface oxide layer on the wafer 106. For example, engineered polypeptides including nonpolar amino acids may selectively bind to hydrophobic defects 150.

In another embodiment, one or more luminescent tags selectively bind to one or more structural defects 150. It is noted herein that structural defects 150 may include, but are not limited to, surface pits, scratches, or crystallographic stacking faults. It is further noted that such structural defects 150 located on a single crystal wafer 106 expose higher Miller index crystal facets, which have higher surface energies than the nominal crystal surface (e.g. a 001 plane of a silicon wafer). Chemisorption of one or more luminescent tags to the one or more structural defects 150 may reduce the surface energy of the wafer 106. In this way, a driving force to minimize surface energy drives the selective binding of one or more luminescent tags may to one or more structural defects 150.

The one or more luminescent tags may include one or more nanoparticles or nanoclusters suitable coupled with a luminescent molecule such as, but not limited to, a fluorophore. It is noted herein that luminescent molecules coupled to nanoparticles less than 5 nm in size may provide a luminescent tag suitable for the detection of correspondingly small defects 150. In one embodiment, one or more luminescent tags selectively bind to defects smaller than 12 nm such that defects smaller than 12 nm may be detected by the system 100. It is further noted that reducing the size of nanoparticles or nanoclusters in a luminescent tag reduces the degree to which the nanoparticles or nanoclusters may quench the luminescence of the luminescent molecule, which correspondingly reduces the constraints on linker molecule length. In one embodiment, one or more luminescent tags include Alexa Fluor® FluoroNanogold™ conjugates.

Referring again to FIG. 1A, in one embodiment, a luminescent tag attachment unit 140 exposes a wafer 106 to luminescent tags in a gas phase. For example, the luminescent tag attachment unit 140 may include a luminescent tag source and a chamber with atmospheric control including, but not limited to, temperature and pressure control such that luminescent tags in a gas phase may be deposited onto one or more wafers 106 within the chamber. In one embodiment, the luminescent tag attachment unit 140 includes a heating element suitable for generating luminescent tags in a gas phase from the luminescent tag source. In another embodiment, the luminescent tag attachment unit 140 includes a source of one or more precursors suitable for reacting in a gas phase to form one or more luminescent tags. In another embodiment, a luminescent tag attachment unit 140 forms one or more luminescent tags through multiple formation stages to generate multiple luminescent tags with different affinities tailored to selectively bind to different defects 150.

In another embodiment, the luminescent tag attachment unit 140 exposes a wafer 106 to luminescent tags in a liquid phase. For example, the luminescent tag attachment unit 140 may include a trough suitable for containing a luminescent tag source in a liquid phase. In one embodiment, the luminescent tag attachment unit 140 includes one or more dipping mechanisms suitable for dipping one or more wafers 106 into the luminescent tag source. In another embodiment, the luminescent tag attachment unit 140 includes a nozzle coupled to the luminescent tag source suitable for spraying a wafer 106 with luminescent tags. In a further embodiment, the luminescent tag attachment unit 140 simultaneously spins a wafer 106 via a rotational stage assembly and sprays one or more luminescent tags on the wafer 106. It is noted that a coupled nozzle and rotation stage may efficiently expose a wafer 106 to one or more luminescent tags such that the required volume of luminescent tag source is minimized.

A luminescent tag attachment unit 140 may expose a wafer 106 to one or more luminescent tags in a single step or through a multi-step process. For example, a luminescent tag attachment unit 140 may expose a wafer 106 to a first type of luminescent tag in a first step, a second type of luminescent tag in a second step, and so forth. As another example, a luminescent tag attachment unit 140 may expose a wafer 106 to any given type of luminescent tag through in a multi-step process. In one embodiment, a wafer 106 is exposed to one or more luminescent tags including a fluorophore, a linker, and a binder through a multi-step process. In a first step, the luminescent tag attachment unit 140 exposes a wafer 106 to a first precursor including a binder, a linker, and a first intermediate binder such that the binder selectively attaches to one or more defects 150 on a wafer 106. In a second step, the luminescent tag attachment unit 140 exposes a wafer 106 to a second precursor including a second intermediate binder and a fluorophore such that the first and second intermediate binders react to form complete luminescent tags including a binder, a linker, and a fluorophore. In this way, chemistry favorable for attaching a binder to one or more defects 150 that may negatively impact the luminescent properties of a luminescent tag may be separated from the attachment of the luminescent molecule to the luminescent tag. It is noted herein that the above examples of multi-step exposure of one or more luminescent tags to a wafer 106 are provided for illustrative purposes and are not intended as limiting and that additional embodiments of a luminescent tag attachment unit 140 configured to expose a wafer 106 to one or more luminescent tags is within the scope and spirit of the present disclosure.

In one embodiment, a luminescent tag attachment unit 140 removes excess luminescent tags from the wafer 106 such that luminescent tags attached to the wafer 106 are selectively bound to one or more defect sites 150 during a detection step. For example, a luminescent tag attachment unit 140 may remove excess luminescent tags not attached to one or more defects through rinsing a wafer 106 with deionized water. A luminescent tag attachment unit 140 may remove excess luminescent tags from the wafer 106 after any or all steps associated with exposing a wafer 106 to one or more luminescent tags.

In one embodiment, the luminescent tag attachment unit 140 is coupled to an inspection chamber 101 via an attachment pathway 142. It is noted herein that the attachment pathway 142 may include one or more wafer 106 handlers suitable for transporting wafers 106 from the luminescent tag attachment unit 140 to the inspection chamber 101.

In one embodiment, the system 100 includes an illumination source 102 configured to generate a beam of illumination 104. The illumination source 102 may include any illumination source known in the art suitable for exciting luminescent tags. For example, the illumination source 102 may include, but is not limited to, any laser system, including one or more laser sources, configured to generate a set of wavelengths or a wavelength range. The laser system may be configured to produce any type of laser radiation such as, but not limited to infrared radiation, visible radiation and/or ultraviolet (UV) radiation. In one embodiment, the illumination source 102 is a laser system configured to emit continuous wave (CW) laser radiation. In another embodiment, the illumination source 102 is a pulsed laser source. In another embodiment, the illumination source 102 is configured to produce a modulated output. For example, the illumination source 102 may be modulated with an acousto-optic or an electro-optic modulator to produce temporally shaped illumination.

It is noted herein that the absorption spectra of one or more luminescent tags overlaps the spectrum of the beam of illumination 104 generated by the illumination source 102. In one embodiment, the absorption spectra of the one or more luminescent tags overlap such that a single narrowband illumination source 102 (e.g. a laser) simultaneously excites all luminescent tags. In another embodiment, a multispectral illumination source 102 simultaneously excites two or more luminescent tags with distinct absorption spectra. A multispectral source may include, but is not limited to, one or more broadband sources or two or more narrowband sources. For example, a multispectral source may include two or more laser systems, wherein the output beams are combined by a beam combiner such as, but not limited to, a diffraction grating, a prism, or a frequency selective dielectric film. In another embodiment, a multispectral source sequentially excites two or more luminescent tags with distinct absorption spectra.

It is noted herein that detecting one or more defects 150 via the collection of illumination emitted from one or more luminescent tags enables the use of a wide range of illumination sources. Any illumination source 102 configured to emit illumination within the absorption spectrum of one or more luminescent tags may be used. This is in contrast to alternative methods of detection (e.g. scattering) wherein the size of the detected defect scales with the wavelength of illumination.

In one embodiment, one or more optical elements 110 direct the beam 104 to a wafer 106. The one or more optical elements 110 may direct the beam 104 to a wafer 106 at any angle of incidence. However, it is noted herein that the reflection of the beam 104 may be dependent on the incidence angle and the polarization of the beam 104. For example, the reflection of a beam 104 polarized in the plane defined by the beam 104 and a surface normal p-polarization (e.g. p-polarization) may be minimized at Brewster's angle. In this way, the electric field strength at the wafer 106 may be maximized at the surface of a wafer 106 in order to maximize the excitation of the luminescent tags. In one embodiment, the one or more optical elements 110 direct the beam 104 to the surface of a wafer 106 at a substantially fixed angle of incidence. In another embodiment, the one or more optical elopements 110 direct the beam 104 to the surface of a wafer 106 at a configurable angle of incidence.

In another embodiment, the system 100 includes a stage assembly 108 suitable for securing and positioning a wafer 106. The stage assembly 108 may include any sample stage architecture known in the art. For example, the stage assembly 108 may include a linear stage. As another example, the stage assembly 108 may include a rotational stage. In one embodiment, the stage assembly 108 includes a chuck suitable for positioning a wafer 106.

The beam 104 may be scanned across the surface of the wafer 106 in order to generate a defect map. In one embodiment, the stage assembly 108 includes a rotational stage to rotate a wafer 106 during illumination. In another embodiment, the one or more illumination optics 110 includes one or more beam scanning optics (not shown) suitable for scanning the beam 104 along a radial direction on the wafer 106. For example, the one or more illumination optics 110 may include any type of beam scanner known in the art such as, but is not limited to, one or more electro-optic beam deflectors, one or more acousto-optic beam deflectors, one or more galvanometric scanners, one or more resonant scanners, or one or more polygonal scanners. In this way, the surface of a wafer 106 may be scanned in an r-theta pattern. It is further noted that the beam 104 may be scanned according to any pattern on the sample. In one embodiment, the beam 104 is split into one or more beams such that one or more beams may be scanned simultaneously.

It is noted herein that a luminescent tag inspection system 100 may operate in either an imaging mode or a non-imaging mode. In an imaging mode, individual objects (e.g. defects) are resolvable within the illuminated spot on the sample. In a non-imaging mode of operation, all of the light collected by one or more detectors is associated with the illuminated spot on the sample. It is further noted that both imaging and non-imaging modes may be applied within the scope and spirit of the present disclosure.

In one embodiment, one or more collection optics 114 collect sample illumination 120 emitted from the wafer 106 and direct the collected illumination 120 to one or more detectors 112. It is noted herein that one or more collection optics 114 may be oriented in any position relative to the wafer 106. In one embodiment, the one or more collection optics 114 includes an objective lens oriented normal to the wafer 106. In another embodiment, the one or more collection optics 114 includes multiple collection lenses oriented to collect illumination 120 from multiple solid angles. In another embodiment, the one or more collection optics 114 includes a pinhole located in a confocal position such that the system 100 may operate as a confocal microscope.

It is noted herein that there may be a temporal offset between the absorption of illumination beam 104 by a luminescent tag and the emission of luminescent illumination 120 by a luminescent tag that may, but is not limited to, range from a nanosecond timescale to a millisecond timescale, based on the luminescent properties of the luminescent particle. For example, a fluorophore emitting fluorescent illumination 120 may have an illumination lifetime on the order of nanoseconds, whereas a phosphorescent molecule may have an illumination lifetime on the order of microseconds to milliseconds. In one embodiment, the one or more collection optics 114 are positioned to capture luminescent emission 120 temporally offset from the absorption of illumination beam 104. For example, the one or more collection optics 114 may interrogate a position of the wafer 106 physically separated along a scan direction. As another example, a scan speed is controlled such that one or more luminescent tags bound to one or more defects 150 remain within a field of view of the one or more collection optics 114 during a lifetime of illumination associated with the one or more luminescent tags.

In one embodiment, one or more optical elements 122 condition the collected illumination 120 prior to detection by the one or more detectors 112. The one or more optical elements 122 may include any elements known in the art suitable for conditioning the collected illumination 120 including, but not limited to, one or more diffractive elements, one or more refractive elements, one or more beam splitters, one or more polarizers, one or more wavelength-selective filters, or one or more neutral density filters. In one embodiment, the one or more optical elements 122 include one or more wavelength-selective filters suitable for passing fluorescent illumination corresponding to the emission spectra of one or more luminescent tags while blocking wavelengths associated with the illumination beam 104. The one or more optical elements 122 may further separate luminescent illumination from one or more distinct emission spectra associated with one or more luminescent tags such that each distinct emission spectra is directed to a separate detector 112. In another embodiment, the one or more optical elements 122 include a diffraction grating configured to physically separate wavelengths associated with the illumination beam 104 from one or more wavelengths associated with the emission spectra of one or more luminescent tags. In another embodiment, the one or more optical elements 122 include one or more wavelength-selective mirrors, wherein each wavelength-selective mirror is configured to direct luminescence associated with a single luminescent tag to a separate detector 112. Further, it is noted herein that the detector 112 may include any optical detector known in the art suitable for measuring illumination received from the wafer 106. For example, the detector 112 may include, but is not limited to, a CCD detector, a TDI detector, a photomultiplier tube (PMT), an avalanche photodiode (APD), or the like. In another embodiment, a detector 112 may include a spectroscopic detector suitable for simultaneously detecting luminescent emission corresponding to the emission spectra of one or more luminescent tags.

It is noted herein that the one or more optical elements 110 and the one or more collection optics 114 may be referred to as a single set of optical elements. It is further noted that the one or more optical elements 110 and the one or more collection optics 114 may share common optical elements. In one embodiment, a single objective lens both directs illumination to the sample and collects illumination from the sample.

In one embodiment, the system 100 includes a controller 130 communicatively coupled to the one or more detectors 112. In one embodiment, the controller 130 includes one or more processors 132. In another embodiment, the one or more processors 132 are configured to execute a set of program instructions maintained in a memory medium 134, or memory.

The one or more processors 132 of a controller 130 may include any processing element known in the art. In this sense, the one or more processors 132 may include any microprocessor-type device configured to execute algorithms and/or instructions. In one embodiment, the one or more processors 132 may consist of a desktop computer, mainframe computer system, workstation, image computer, parallel processor, or any other computer system (e.g., networked computer) configured to execute a program configured to operate the system 100, as described throughout the present disclosure. It is further recognized that the term "processor" may be broadly defined to encompass any device having one or more processing elements, which execute program instructions from a non-transitory memory medium 134. Therefore, the above description should not be interpreted as a limitation on the present invention but merely an illustration.

The memory medium 134 may include any storage medium known in the art suitable for storing program instructions executable by the associated one or more processors 132. By way of a non-limiting example, the memory medium 134 may include a non-transitory memory medium. By way of additional non-limiting examples, the memory medium 134 may include, but is not limited to, a read-only memory, a random access memory, a magnetic or optical memory device (e.g., disk), a magnetic tape, a solid state drive and the like. It is further noted that memory 134 may be housed in a common controller housing with the one or more processors 132. In an alternative embodiment, the memory 134 may be located remotely with respect to the physical location of the one or more processors 132 and controller 130. For instance, the one or more processors 132 of controller 130 may access a remote memory (e.g., server), accessible through a network (e.g., internet, intranet and the like).

In one embodiment, the one or more processors 132 are configured to execute program instructions configured to direct the one or more processors 132 to identify one of more defects 150 on a wafer 106 based on the collected illumination 120. For example, the one or more processors 132 may be configured to generate a defect map of the surface of the wafer 106 including one or more identified defects 150. In another embodiment, the controller 130 is further communicatively coupled to the stage assembly 108 to associated collected illumination 120 with specific locations on the sample associated with one or more defects 150.

A luminescent tag based inspection system 100 may detect the size and/or shape of one or more defect sites 150 according to the number and density of luminescent tags bound to the one or more defect sites 150. For example, configuring the luminescent tags to fully cover the surface are of the particle may enable detection of the size and/or shape of the one or more defect sites.

It is noted herein that the resolution of the system 100 is, in part, related to the diffraction-limited optical resolution of the one or more collection optics 114. Defects 150 larger than the diffraction-limited optical resolution of the system 100 may be fully resolvable, enabling the size and shape of the defects 150 to be accurately determined. However, one or more luminescent molecules on a defect 150 smaller than the diffraction-limited optical resolution of the system 100 are imaged to a size of the diffraction-limited optical resolution. However, the signal strength may be proportional to the surface area. In this way, the size of a defect smaller than the diffraction-limited optical resolution of the system 100 may be determined.

The resolution of a defect map may additionally be increased beyond the diffraction-limited optical resolution of the system 100 by applying super-resolution techniques including, but not limited to, photo-activated localization microscopy (PALM) stimulated emission depletion (STED) microscopy, or stochastic optical reconstruction microscopy (STORM). In this way, luminescent molecules such as, but not limited to, fluorophores emit luminescence stochastically such that neighboring luminescent molecules separated by less than the diffraction-limited optical resolution of the system 100 do not emit simultaneously. The one or more processors 132 may then be configured to execute program instructions configured to direct the one or more processors 132 to perform localization analysis of multiple defect maps associated with multiple scans of the wafer 106 such that the position of luminescent molecules may be calculated with a precision greater than the diffraction-limited optical resolution of the system. For example, a luminescent smaller than the diffraction-limited optical resolution of the system 100 may be imaged onto a detector 112 with a size equal to the diffraction-limited spot size; a localization analysis may filter then image such that only the centroid of the diffraction-limited spot size is associated with the position of the luminescent. In this way, a defect map may have a resolution greater than the diffraction-limited optical resolution of the system 100.

In one embodiment, a luminescent tag removal unit 144 is coupled to the inspection chamber 101 by an attachment pathway 146. It is noted herein that the attachment pathway 146 may include one or more wafer handlers suitable for transporting wafers 106 from the luminescent tag removal unit 140 to the inspection chamber 101. In one embodiment, the luminescent tag removal unit 144 includes one or more troughs suitable for holding one or more solvents.

In another embodiment, the luminescent tag removal unit 144 exposes a wafer 106 to one or more solvents to remove luminescent tags. For example, the luminescent tag removal unit 144 may include one or more troughs suitable for containing one or more solvents. In one embodiment, the luminescent tag removal unit 144 includes one or more dipping mechanisms suitable for dipping one or more wafers 106 into the solvents. In a further embodiment, the luminescent tag removal unit 144 simultaneously spins a wafer 106 via a rotational stage assembly and sprays one or more luminescent tags on the wafer 106. It is noted that a coupled nozzle and rotation stage may efficiently expose a wafer 106 to one or more luminescent tags such that the required volume of solvent is minimized. It is noted herein that the one or more solvents may include any solvent suitable for removing luminescent tags from the surface of a wafer including, but not limited to, deionized water, ammonium hydroxide ($NH_4OH$), hydrogen peroxide ($H_2O_2$), a "piranha solution" ($H_2O_2$:$H_2SO_4$), hydrochloric acid (HCL), hydrofluoric acid (HF), TCEP (tris-(2-carboxyethyl)phosphine or P(CH2CH2COOH)3), or DTT (dithiolthreitol or IUPAC name 1,4-dimercapto-2,3-butanediol). It is further noted that TCEP or DTT may be particularly suitable for breaking disulfide bonds associated with one or more luminescent tags bound to polymer, organic, or bioorganic defects 150.

In one embodiment, the luminescent tag removal unit 144 is configured to perform an "RCA" clean including of a first step of removing organic molecules with a solution of ammonium hydroxide and hydrogen peroxide (e.g. "standard clean 1" or SC-1), a second step of removing surface oxides with a solution of hydrofluoric acid, and a third step of removing ionic compounds with a solution of hydrochloric acid and hydrogen peroxide (e.g. "standard clean 2" or SC-2). It is noted herein that luminescent tags may be removed through exposure to ozone. In one embodiment, the luminescent tag removal unit 144 includes an illumination source configured to generate illumination in the ultraviolet spectrum suitable for generating ozone from ambient air. In one embodiment, the luminescent tag removal unit 144 includes a heat source suitable for dissociating one or more bonds within the one or more luminescent tags. For example, a luminescent tag removal unit 144 may remove one or more luminescent tags attached to one or more defects 150 by breaking down or volatizing the one or more luminescent tags. In another embodiment, a luminescent tag removal unit 144 removes one or more luminescent tags through plasma cleaning. For example, a luminescent tag removal unit 144 may include a chamber suitable for controlling the composition and pressure of the atmosphere surrounding a wafer 106 and a plasma ignition source configured to generate a plasma within the chamber. In this way, the one or more luminescent tags may be dissociated. The composition of the atmosphere associated with the plasma may be, but is not limited to, oxygen or argon.

Figure 4:
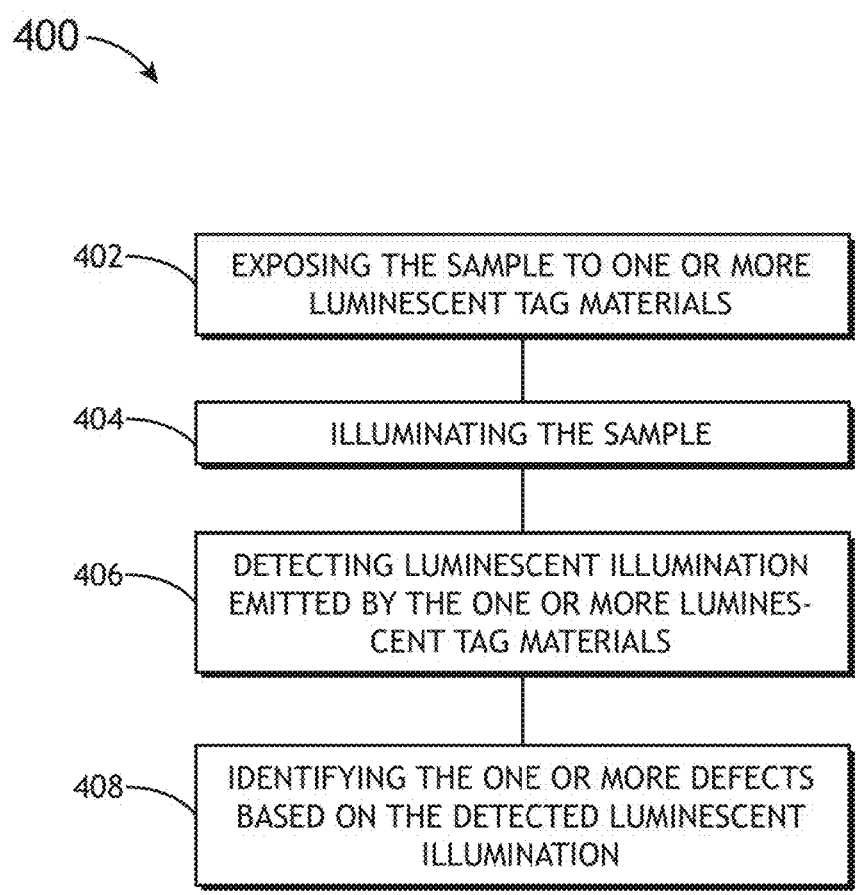
FIG. 4 is a flow diagram illustrating the detection of defects on a sample using luminescent tag materials, in accordance with one or more embodiments of the present disclosure.

FIG. 4 is a flow diagram illustrating a method 400 to detect defects using luminescent tag materials, in accordance with one or more embodiments of the present disclosure. In step 402, a sample 106 (e.g. a wafer) is exposed to one or more luminescent tag materials. The one or more luminescent tag materials absorb illumination within one or more absorption spectra and emit illumination within one or more emission spectra. The one or more luminescent tag materials selectively attach to one or more defects 150 on the sample 106. In this way, the one or more luminescent tag materials preferentially attach to the one or more defects 150 and not to the surrounding sample 106. In step 404, the sample 106 is illuminated with one or more wavelengths of illumination corresponding to the one or more absorption spectra. In step 406, luminescent illumination emitted by the one or more luminescent tag materials is detected. In step 408, one or more defects 150 are identified based on the detected luminescent illumination. For example, one or more defects 150 may be identified by generating a defect map of the surface of the wafer 106 on which the one or more identified defects 150 are identified.

It is noted herein that the luminescent tag attachment unit 140 and the luminescent tag removal unit 144 may be associated with a single luminescent tag manipulation device. It is further noted that the description of the luminescent tag removal unit 144 is intended to be illustrative rather than limiting and that some embodiments do not include a luminescent tag removal unit 144. For example, a luminescent tag based inspection system 100 may operate on sacrificial samples to detect one or more defects 150 without removing the luminescent tags. In this way, a system 100 may detect adder particles associated with a semiconductor fabrication device on a sacrificial wafer without risk of contaminating additional fabrication devices.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the disclosure is defined by the appended claims.

What is claimed is:

1. A luminescent tag based defect detection system, comprising:
    a luminescent tag attachment assembly containing one or more luminescent tag materials, wherein the luminescent tag attachment assembly is configured to expose a sample to the one or more luminescent tag materials, wherein the one or more luminescent tag materials absorb illumination within one or more absorption spectra and emit illumination within one or more emission spectra, wherein the one or more luminescent tags selectively attach to one or more defects on the sample;
    an illumination source configured to generate illumination including one or more wavelengths corresponding to the one or more absorption spectra;
    one or more detectors;
    a set of optical elements, wherein at least a portion of the set of optical elements directs illumination from the illumination source to the sample, wherein at least a portion of the set of optical elements collects illumination from the sample, wherein at least a portion of the set of optical elements directs illumination emitted from the one or more luminescent tag materials to the one or more detectors; and
    a luminescent tag removal assembly configured to receive the sample from the inspection chamber, wherein the luminescent tag removal assembly is configured to remove the one or more luminescent tag materials from the sample following inspection of the sample.

2. The system of claim 1, wherein one or more luminescent tag materials preferentially attach to the one or more defects.

3. The system of claim 2, wherein the one or more luminescent tag materials do not attach to a surface of the sample.

4. The system of claim 1, wherein the one or more luminescent tag materials include one or more fluorophores.

5. The system of claim 1, wherein the one or more luminescent tag materials include one or more phosphorescent molecules.

6. The system of claim 1, wherein the one or more emission spectra are different than the one or more absorption spectra.

7. The system of claim 1, wherein the luminescent tag attachment assembly comprises:
    a heating element configured to generate a gas phase of the one or more luminescent tag materials such that the sample is exposed to a gas phase of the one or more luminescent tag materials.

8. The system of claim 1, wherein the luminescent tag attachment assembly comprises:
    one or more nozzles configured to expose the sample to a liquid phase of the one or more luminescent tag materials.

9. The system of claim 8, wherein the luminescent tag attachment assembly further comprises:
    a rotation stage assembly configured to rotate the sample during exposure to a liquid phase of the one or more luminescent tag materials.

10. The system of claim 1, wherein the luminescent tag attachment unit is further configured to expose the sample to a reducing agent to remove one or more oxide layers from the one or more defects prior to the expose of a sample to one or more luminescent tag materials.

11. The system of claim 1, wherein the luminescent tag attachment unit is further configured to remove excess luminescent tag materials not bound to the one or more defects after the expose a sample to one or more luminescent tag materials.

12. The system of claim 1, wherein at least one of the one or more luminescent tag materials include one or more nanoparticles, one or more nanoclusters, one or more proteins, one or more phages, one or more thiols, or one or more peptides.

13. The system of claim 1, wherein the at least one of the one or more luminescent tags comprises:
    a luminescent molecule, and a binder molecule.

14. The system of claim 13, wherein the binder molecule includes at least one of a thiol, a polypeptide, or a nanoparticle.

15. The system of claim 14, wherein a polypeptide comprises:

a dodecapeptide, wherein the dodecapeptide comprises at least one of AuBP1 or AuBP2, wherein AuBP1 comprises an amino acid sequence of WAGAKRLVLRRE, wherein AuBP2 comprises an amino acid sequence of WALRRSIRRQSY, wherein W corresponds to tryptophan, A corresponds to tlanine, G corresponds to glycine, K corresponds to lysine, R corresponds to arginine, L corresponds to leucine, V corresponds to valine, E corresponds to glutamic acid, S corresponds to serine, I corresponds to isoleucine, Q corresponds to glutamine, and Y corresponds to tyrosine.

16. The system of claim 1, wherein the at least one of the one or more luminescent tag materials further comprise:
a linker molecule.

17. The system of claim 16, wherein the linker molecule comprises:
alkanethiols, wherein the number of alkyl groups is in the range of 4 to 16.

18. The system of claim 16, wherein at least one luminescent tag comprises:
4-methylcoumarin-PEG-thiol.

19. The system of claim 1, wherein the one or more defects include at least one of one or more particles, one or more organic molecules, or one or more structural defects.

20. The system of claim 19, wherein the one or more particles comprise:
at least one of gold, silver, or copper.

21. The system of claim 1, wherein a size of at least one of the one or more defects is determined by an intensity of illumination emitted from one or more luminescent tag materials attached to the at least one of the one or more defects.

22. The system of claim 1, wherein the size of the one or more luminescent tags is less than 10 nm.

23. The system of claim 1, wherein the size of the one or more defects is less than 12 nm.

24. The system of claim 1, wherein the one or more luminescent tag materials are selectively attached to the one or more defects in at least one of a monolayer, a bilayer, or a multilayer arrangement.

25. The system of claim 1, wherein the luminescent tag removal assembly comprises:
one or more nozzles configured to expose the sample to one or more solvents.

26. The system of claim 25, wherein the luminescent tag removal assembly further comprises:
a rotation stage assembly configured to rotate the sample during exposure to a liquid phase of the one or more luminescent tag materials.

27. The system of claim 25, wherein the one or more solvents include at least one of deionized water, ammonium hydroxide, hydrogen peroxide, a piranha solution, hydrochloric acid, hydrofluoric acid, tris-(2-carboxyethyl)phosphine, or dithiolthreitol.

28. The system of claim 1, wherein the luminescent tag removal assembly comprises:
an illumination source configured to emit ultraviolet illumination with wavelengths in the ultraviolet spectrum, wherein the ultraviolet illumination generates ozone to oxidize at least one of the luminescent tag materials.

29. The system of claim 1, wherein the luminescent tag removal assembly comprises:
a chamber configured to control a composition and a pressure of a gas surrounding the sample; and
a plasma ignition source to ignite the gas surrounding the sample into a plasma.

30. The system of claim 29, wherein the gas comprises:
at least one of oxygen or argon.

31. The system of claim 1, further comprising a controller, wherein the controller is communicatively coupled to the detector, the controller including one or more processors configured to execute program instructions configured to cause the one or more processors to generate a defect map based on collected illumination within one or more emission spectra.

* * * * *